(12) United States Patent
Acker

(10) Patent No.: US 6,211,666 B1
(45) Date of Patent: Apr. 3, 2001

(54) OBJECT LOCATION SYSTEM AND METHOD USING FIELD ACTUATION SEQUENCES HAVING DIFFERENT FIELD STRENGTHS

(75) Inventor: David E. Acker, Setauket, NY (US)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/117,801
(22) PCT Filed: Feb. 24, 1997
(86) PCT No.: PCT/US97/02499
§ 371 Date: Dec. 10, 1998
§ 102(e) Date: Dec. 10, 1998
(87) PCT Pub. No.: WO97/32179
PCT Pub. Date: Sep. 4, 1998

Related U.S. Application Data
(60) Provisional application No. 60/012,326, filed on Feb. 27, 1996.

(51) Int. Cl.[7] .............. G01B 7/14; G01B 33/02; A61B 5/05
(52) U.S. Cl. .............. 324/207.17; 324/207.26; 128/899; 600/424
(58) Field of Search .......... 324/207.17, 207.23, 324/207.24, 207.25, 207.26, 243; 128/899; 600/424; 702/150, 152, 153; 342/448

(56) References Cited

U.S. PATENT DOCUMENTS

| | | |
|---|---|---|
| 3,644,825 | 2/1972 | Davis, Jr. et al. ............. 324/41 |
| 3,868,565 | 2/1975 | Kuipers ..................... 324/34 R |
| 4,017,858 | 4/1977 | Kuipers ..................... 343/100 R |
| 4,054,881 | 10/1977 | Raab ........................ 343/112 R |
| 4,560,930 | 12/1985 | Kouno ....................... 324/207 |
| 4,570,354 | 2/1986 | Hindes ...................... 33/534 |
| 4,592,356 | 6/1986 | Gutierrez ................... 128/339 |

(List continued on next page.)

FOREIGN PATENT DOCUMENTS
| | | |
|---|---|---|
| WO 94/00050 | 1/1994 | (WO). |
| WO 94/04938 | 3/1994 | (WO). |
| WO 94/06349 | 3/1994 | (WO). |

(List continued on next page.)

OTHER PUBLICATIONS

"Effects of laser irradiation delivered by flexible fiberoptic system on the left ventricular internal myocardium" American Heart Journal, Sep. 1983, pp. 587–590.

Dorothy Bonn, "High–Power laser help the Ischaemic Heart", The Lancet, vol. 348 (Jul. 13, 1996) p. 118.

Mahmood Mirhoseini et al. "Transmyocardial Laser Revascularization: A Review" Journal of Clinical Laser Medicine & Surgery. vol. 11(1993) pp. 15–19.

Mahmood Mirhoseini et al. "Transmyocardial Laser Revascularization: A Review" Journal of Clinical Laser Medicine & Surgery. vol. 11(1993) pp. 15–19.

Primary Examiner—Walter E. Snow
(74) Attorney, Agent, or Firm—Louis J. Capezzuto

(57) ABSTRACT

A method and system of operating a location system to locate objects in space, such as medical instruments (16) within the body of a patient is presented. The method includes cyclically actuating transmitters (10a, 10b, 10c) in a fixed frame of reference for the transmission of magnetic fields to a plurality of sensing units (54a, 54b, 54c). The sensing units detect characteristics of the fields during actuation sequences for determining location. At least one transmitter may be actuated during at least some of the cycles in a plural-value actuation sequence to provide a field with different field strengths during a sequence of plural sensing intervals, and with a progressively varying field strength value during transition intervals between the sensing intervals.

30 Claims, 4 Drawing Sheets

U.S. PATENT DOCUMENTS

| | | | |
|---|---|---|---|
| 4,613,866 | 9/1986 | Blood | 343/448 |
| 4,642,786 | 2/1987 | Hansen | 364/559 |
| 4,651,436 | 3/1987 | Gaal | 33/533 |
| 4,710,708 | 12/1987 | Rorden et al. | 324/207 |
| 4,788,987 | 12/1988 | Nickel | 128/777 |
| 4,849,692 | 7/1989 | Blood | 324/208 |
| 4,869,238 | 9/1989 | Opie et al. | 128/6 |
| 4,905,698 | 3/1990 | Strohl, Jr. et al. | 128/653 R |
| 4,917,095 | 4/1990 | Fry et al. | 128/600.03 |
| 4,921,482 | 5/1990 | Hammerslag et al. | 604/95 |
| 4,931,059 | 6/1990 | Markham | 606/185 |
| 4,945,305 | 7/1990 | Blood | 324/207.117 |
| 5,002,137 | 3/1991 | Dickinson et al. | 175/19 |
| 5,042,486 | 8/1991 | Pfeiler et al. | 128/653 R |
| 5,059,197 | 10/1991 | Urie et al. | 604/164 |
| 5,078,144 | 1/1992 | Sekino et al. | 128/660.03 |
| 5,099,845 | 3/1992 | Besz et al. | 128/653.1 |
| 5,125,924 | 6/1992 | Rudko | 606/12 |
| 5,125,926 | 6/1992 | Rudko et al. | 606/19 |
| 5,158,084 | 10/1992 | Ghiatas | 128/657 |
| 5,172,056 | 12/1992 | Voision | 324/207.17 |
| 5,195,540 | 3/1993 | Shiber | 128/898 |
| 5,195,968 | 3/1993 | Lundquist et al. | 604/95 |
| 5,197,482 | 3/1993 | Rank et al. | 128/749 |
| 5,211,165 | 5/1993 | Dumoulin et al. | 128/653.1 |
| 5,215,680 | 6/1993 | D'Arrigo | 252/307 |
| 5,217,484 | 6/1993 | Marks | 606/200 |
| 5,234,426 | 8/1993 | Rank et al. | 606/1 |
| 5,251,635 | 10/1993 | Dumoulin et al. | 128/653.1 |
| 5,253,647 | 10/1993 | Takahashi et al. | 128/653.1 |
| 5,255,680 | 10/1993 | Darrow et al. | 128/653.1 |
| 5,265,610 | 11/1993 | Darrow et al. | 128/653.1 |
| 5,267,960 | 12/1993 | Hayman et al. | 604/106 |
| 5,273,025 | 12/1993 | Sakiyama et al. | 128/6 |
| 5,275,166 | 1/1994 | Vaitekunas et al. | 128/660.03 |
| 5,295,484 | 3/1994 | Marcus et al. | 128/660 |
| 5,295,486 | 3/1994 | Wollschager et al. | 128/661.01 |
| 5,301,682 | 4/1994 | Debbas | 128/737 |
| 5,309,913 | 5/1994 | Kormas et al. | 128/653 |
| 5,325,897 | 7/1994 | Hirschi et al. | 128/899 |
| 5,368,564 | 11/1994 | Savage | 604/95 |
| 5,368,592 | 11/1994 | Stern et al. | 606/33 |
| 5,373,849 | 12/1994 | Maroney et al. | 128/662 |
| 5,375,596 | 12/1994 | Twiss et al. | 128/653.1 |
| 5,377,678 | 1/1995 | Dumoulin et al. | 128/653.1 |
| 5,380,316 | 1/1995 | Aita et al. | 606/7 |
| 5,383,454 | 1/1995 | Bucholz | 128/653.1 |
| 5,383,874 | 1/1995 | Jackson et al. | 606/1 |
| 5,383,923 | 1/1995 | Webster, Jr. | 607/125 |
| 5,385,148 | 1/1995 | Lesh et al. | 128/662.06 |
| 5,389,096 | 2/1995 | Aita et al. | 606/15 |
| 5,391,199 | 2/1995 | Ben Haim | 607/122 |
| 5,403,356 | 4/1995 | Hill et al. | 607/14 |
| 5,404,297 | 4/1995 | Birk et al. | 362/421 |
| 5,409,004 | 4/1995 | Sloan | 128/657 |
| 5,423,321 | 6/1995 | Fontenot | 128/664 |
| 5,425,367 | 6/1995 | Shapiro et al. | 128/653 |
| 5,425,382 | 6/1995 | Golden et al. | 128/899 |
| 5,429,132 | 7/1995 | Guy et al. | 128/653.1 |
| 5,431,168 | 7/1995 | Webster et al. | 128/658 |
| 5,433,198 | 7/1995 | Desai | 128/642 |
| 5,437,277 | 8/1995 | Dumoulin et al. | 128/653.1 |
| 5,443,489 | 8/1995 | Ben-Haim | 607/115 |
| 5,450,846 | 9/1995 | Goldreyer | 128/642 |
| 5,465,717 | 11/1995 | Imran et al. | 128/642 |
| 5,471,982 | 12/1995 | Edwards et al. | 128/642 |
| 5,471,988 | 12/1995 | Fujio et al. | 128/660.03 |
| 5,480,422 | 1/1996 | Ben-Haim | 607/122 |
| 5,483,951 | 1/1996 | Frassica et al. | 600/104 |
| 5,487,391 | 1/1996 | Panescu | 128/699 |
| 5,538,008 | 7/1996 | Crowe | 128/751 |
| 5,554,152 | 9/1996 | Aita et al. | 606/7 |
| 5,555,883 | 9/1996 | Avitall | 128/642 |
| 5,558,091 | 9/1996 | Acker et al. | 128/653.1 |
| 5,558,092 | 9/1996 | Unger et al. | 128/660.03 |
| 5,577,502 | 11/1996 | Darrow et al. | 128/653.1 |
| 5,588,432 | 12/1996 | Crowley | 128/660.03 |
| 5,617,857 | 4/1997 | Chader et al. | 128/653.1 |
| 5,622,169 | 4/1997 | Golden et al. | 128/653.1 |
| 5,715,822 | 2/1998 | Watkins et al. | 128/653.5 |
| 5,729,129 | 3/1998 | Acker | 324/207.12 |

FOREIGN PATENT DOCUMENTS

| | | |
|---|---|---|
| WO 94/23647 | 10/1994 | (WO) . |
| WO 94/28782 | 12/1994 | (WO) . |
| WO 95/05773 | 3/1995 | (WO) . |
| WO 95/07657 | 3/1995 | (WO) . |
| WO 95/09562 | 4/1995 | (WO) . |
| WO 95/10226 | 4/1995 | (WO) . |
| WO 95/19738 | 7/1995 | (WO) . |
| WO 96/05768 | 2/1996 | (WO) . |
| WO 96/41119 | 12/1996 | (WO) . |
| WO 97/03609 | 2/1997 | (WO) . |
| WO 97/29678 | 8/1997 | (WO) . |
| WO 97/29679 | 8/1997 | (WO) . |
| WO 97/29683 | 8/1997 | (WO) . |
| WO 97/29684 | 8/1997 | (WO) . |
| WO 97/29685 | 8/1997 | (WO) . |
| WO 97/29701 | 8/1997 | (WO) . |
| WO 97/29709 | 8/1997 | (WO) . |
| WO 97/29710 | 8/1997 | (WO) . |
| WO 97/29803 | 8/1997 | (WO) . |
| WO 97/32179 | 9/1997 | (WO) . |

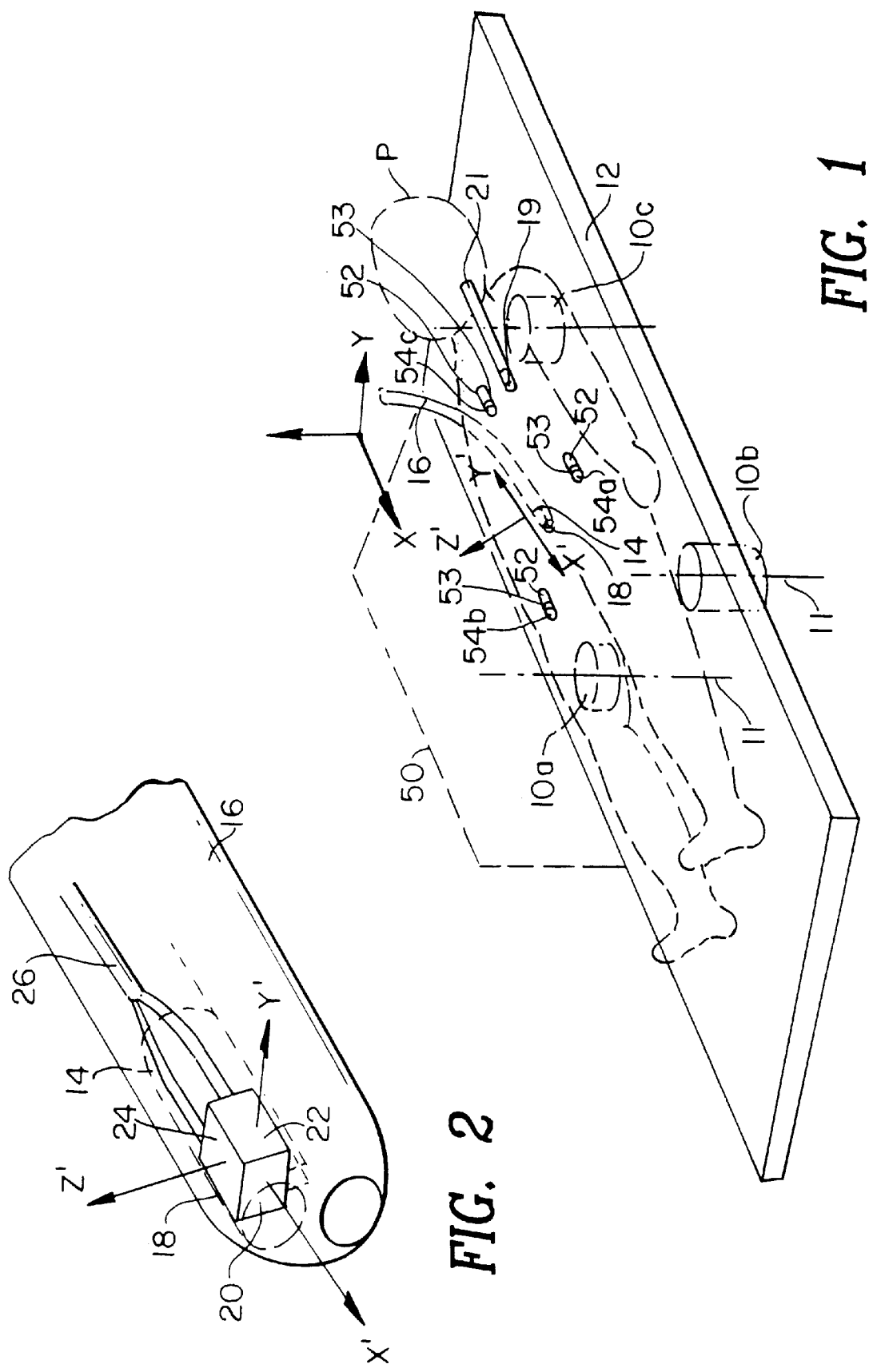

OBJECT LOCATION SYSTEM AND METHOD USING FIELD ACTUATION SEQUENCES HAVING DIFFERENT FIELD STRENGTHS

CROSS-REFERENCE TO RELATED APPLICATIONS

The present application claims benefit of United States Provisional Application No. 60/012,326, filed Feb. 27, 1996, the disclosure of which is hereby incorporated by reference herein.

TECHNICAL FIELD

Various systems have been proposed for detecting the position and/or orientation of an object using magnetic or electromagnetic fields. These systems typically employ field transmitters, such as electromagnet coils, disposed at known locations in a fixed reference frame and a sensor, such as a coil or other transducer mounted to the object to be located. Each transmitter projects a field varying in space in a fixed frame of reference. The pattern of variation in space for each transmitter is different than the pattern for each other transmitter. For example the transmitters may be identical to one another but disposed at different locations or in different orientations. The field patterns of the transmitters are thus displaced or rotated relative to one another and relative to the fixed frame of reference. The sensor on the object includes one or more sensing elements for detecting the parameters of the field prevailing at the location of the object as, for example, the magnitude and/or direction of the field at the object or the magnitudes of individual components of the field at the object in one or more preselected local directions defined with reference to the sensor. The transmitters may be actuated in a predetermined sequence so that at any time only one transmitter is active and therefore the field prevailing at the object is only the field contributed by one transmitter, plus a background field due to the Earth's magnetic field and other environmental sources. Based upon the detected parameters of the fields from the individual transmitters, and the known pattern of variation of the field from each transmitter, a computer system calculates the position and orientation of the sensor, and hence the position of the object bearing the sensor, in the fixed frame of reference of the transmitters. In a variant of this system, the object to be located carries the transmitter or transmitters, whereas a plurality of sensing elements are disposed at various locations or orientations in the fixed frame of reference. The location and/or orientation of the object is deduced from signals representing the parameters of the field prevailing at the various sensors.

Systems of this general nature are disclosed in U.S. Pat. Nos. 4,849,692; 4,642,786; 4,710,708; 4,613,866 and 4,945,305. Systems according to this general design can be used to provide a three-dimensional spatial input capability for a computer. Another system of this nature is disclosed in International Patent publication WO 94/04938. In the '938 publication, the object to be located may be a medical endoscope. Such a system may include a sensor mounted on the tip of an endoscope, so that the location and/or orientation of the endoscope tip can be determined while the sensor is disposed inside the body of a medical patient. Other systems for locating medical instruments such as endoscopes and catheters based upon transmitted fields are disclosed in U.S. Pat. Nos. 5,042,486; 5,099,845; 5,211,165; 5,251,635; 5,253,647; 5,255,680; 5,265,610 and 5,391,199.

Typical sensing elements have limited operating ranges. For example, a sensing element such as a magnetoresistive or Hall-effect device adapted to provide an electrical signal representing the magnitude of a magnetic field component in a particular direction typically provides the most accurate signals when the field component magnitude lies within a relatively narrow range. As described in copending, commonly-assigned United States Patent Application U.S. Ser. No. 08/476,380 (now issued as U.S. Pat. No. 5,729,129 on Mar. 17, 1998) and in PCT Application PCT/US96/08411, entitled MAGNETIC LOCATION SYSTEM WITH ADAPTIVE FEEDBACK CONTROL, the disclosures of which are hereby incorporated by reference herein, a magnetic location system may be provided with feedback control to adjust the operation of the field transmitters responsive to the signals from the sensing elements. For example, a locating system may incorporate several multielement sensors, each including several different sensing elements for detecting field components in several different directions. Each sensor may be mounted to a different object. For example, one sensor may be mounted to a medical instrument, whereas another sensor may be mounted to the patient's body, so that the system can track the locations of the instrument and the body simultaneously. Where a first sensor is close to a first field transmitting coil, and far from a second field transmitting coil, and both coils are driven in the same way to produce fields of equal overall magnitude, the magnitudes of all of the magnetic field components detected by the sensing elements will be higher during operation of the first coil than during operation of the second coil. For a similar second sensor disposed adjacent the second coil and remote from the first coil, the signals will be higher during operation of the second coil.

According to preferred embodiments of the '380 application, actuation of the coils is controlled in response to the signals from the sensing elements to keep the field components at the sensing element within desired ranges. Some systems disclosed in the '380 application operate cyclically. During each cycle of operation, each coil is actuated during a plurality of separate sensing intervals. During each sensing interval, one sensor is operated and the other sensors are inactive. For example, where a system includes two sensors 1 and 2, and three coils denominated A,B and C, the cycle may include a first sensing interval A1 in which coil A is activated and sensor 1 is operated to acquire a signal, followed by a second sensing interval in A2 in which coil A is activated and sensor 1 is operated, and so on so that the oval cycle includes intervals A1,A2,B1,B2, C1,C2. During each cycle, the signal acquired from sensor 1 in the previous cycle is used to adjust the currents applied to the various coils in intervals A1,B1 and C1, whereas the signal acquired from sensor 2 in the previous cycle is used to adjust the currents applied in intervals A2,B2,C2. In this way, the magnitude of the magnetic field impinging on sensor 1 during intervals A1,B1,C1 will be maintained within the operating range of sensor 1, whereas the magnitude of the magnetic field impinging on sensor 2 during intervals A2,B2,C2 will be maintained within the operating range of sensor 2. A control computer system keeps track of the currents used during each cycle, and hence the magnitudes of the magnetic fields applied by each coil. This information is factored into the equations used to derive position and orientation information for each sensor from the readings of the sensing elements. The actual current applied to each coil during each sensing interval will vary with the position of the sensor associated with such interval.

Where more sensors are used, more sensing intervals can be added to the cycle. The number of sensing intervals in the entire cycle may be equal to the product of the number of sensors and the number of coils. Also, in a system according to a further refinement also taught in the '380 application, separate sensing intervals, and separate coil current settings, may be provided for each sensing element in a multielement sensor. Thus, the magnetic field strength provided by each coil is adjusted separately for each sensing element, so that the field component in the direction associated with a particular sensing element will be within the desired range of that element. In such a system, the number of sensing intervals can be equal to the number of individual sensing elements times the number of coils.

The use of feedback control according to these embodiments of the '380 application provides significant improvements in accuracy, and allows the use of sensors which have limited operating range but which provide other significant advantages such as compactness. However, appreciable time is required to increase the current in each coil to the desired current level at the beginning of each sensing interval. The time required for the current to increase is commonly referred to as "risetime". Also, when the magnetic field strength applied by a coil is increased or decreased, eddy currents are induced in electrically conductive materials in or near the system. The eddy currents superimpose spurious magnetic fields on the fields to be sensed. Therefore, the control system may delay acquisition of the signals from the sensing elements for an appreciable time after the current in a coil reaches the desired value for a particular sensing interval. This delay time, commonly referred to as "settling" time, allows time for the eddy currents to dissipate. Because risetime and settling time have been added to each sensing interval in time-division-multiplexed embodiments taught in the '380 application, the time required for each cycle has been appreciably longer than that required for a comparable cycle with only one actuation of each coil. Longer cycle times reduce the ability of the system to keep track of rapidly-changing sensor locations.

Accordingly, it would be desirable to provide improved location methods and apparatus which allow for actuation of each transmitter to multiple field strengths during a cycle, but which alleviate the delays occasioned by rise time and settling time.

DISCLOSURE OF THE INVENTION

The present invention addresses these needs.

One aspect of the present invention provides methods of operating a location system such as a magnetic location system which includes at least one transmitter and which also includes a plurality of sensing units adapted to detect the field from such transmitter or transmitters. Stated another way, if a particular transmitter, such as an electromagnetic coil, must provide three different values during three different sensing intervals, the coil is not turned off after the first sensing interval. Rather, the magnetic field strength provided by such transmitter or coil is progressively varied to the value required for the next sensing interval, following after the adjustment interval.

The sensing field strengths applied during the sensing intervals of each plural value actuation sequence are ordered progressively, and most preferably from a lowest value to a highest value. Thus, during each cycle of operation, each transmitter or coil is driven first with the lowest-magnitude field strength to be applied by that transmitter during that particular cycle; then with the next higher field strength and so on until the highest field strength to be applied in that cycle by that transmitter in the particular cycle is reached. In this arrangement, the change in field strength which must be accomplished during any transition interval between sensing intervals is always less than the change which would be required to bring the electromagnet from a full off or zero field strength condition to the next required field strength. Because the required rise time and settling time for a change in field strength are directly related to the magnitude of the change, the rise time and settling time required will be considerably less than that which would be required if the transmitter were switched off between sensing intervals.

In those systems which employ the feedback control invention of the '380 application, the field strength required for application during operation of a particular sensing unit may vary during operation of the system. Thus, as a particular sensor moves away from a particular transmitter, the field strength required for such transmitter during operation of that particular sensor will generally increase. To accommodate such changes, the method desirably includes the step of automatically reordering sensing intervals associated with different sensing units as the required field strengths for such sensing intervals change. Thus, the order of operation of the sensing units is varied so that the field strengths applied during the various sensing intervals of each plural value actuation sequence remain in the desired progressive order.

The method may further include the step of dynamically grouping or ungrouping units during operation so that sensing units which are operated during separate sensing intervals with a particular transmitter during some cycles can be operated during a single sensing interval with the same transmitter during other cycles. The sensors are grouped or ungrouped for operation with each transmitter on each cycle depending upon the field strength required from the transmitter for the particular sensing unit. Thus, where the difference between the field strengths required for optimum operation of two or more sensing elements or sensors during a particular cycle is less than a preselected threshold, both sensors or sensing elements can be grouped together and operated during a single sensing interval, with a single field strength close to both of the optimum field strengths. However, where the field strengths required from a particular transmitter for the same sensors or sensing elements during a different cycle are markedly different from one another, the transmitter can be actuated in a plural-valued sequence as discussed above to provide different sensing intervals with different field strengths for each sensor or sensing element. This mode of operation reduces the number of sensing intervals required and thus, further shortens cycle times.

Depending upon the locations and orientations of the sensors or sensing elements, some or all of the electromagnets or other transmitters may be operated with only a single field strength during a particular cycle and, therefore, may be operated in a single-vai actuation sequence to provide a single sensing interval. Thus, depending upon the positions and orientations of the sensors, a particular cycle may include plural-value actuation sequences for all of the transmitters; plural-value actuation sequences for some transmitter and single value sequences for the others or all single value sequences.

A further aspect of the invention provides location apparatus such as magnetic location apparatus. Apparatus according to this aspect of the invention includes at least one transmitter, such as an electromagnet, and one or more sensing units operative to detect characteristics of fields impinging thereon. The apparatus also includes a driver operative to actuate the transmitters cyclically, so that during each cycle of actuation each transmitter is actuated in a preselected actuation sequence and so that at least one transmitter is actuated during at least some cycles in a plural value actuation sequence as aforesaid, to provide different magnetic field strengths during a sequence of plural sensing intervals and to provide a progressively varying magnetic field strength during adjustment intervals between the sensing intervals. Apparatus according to this aspect of the invention can provide advantages similar to those discussed above in connection with the method. Preferably, the apparatus includes a control computer and one or more actuators connected to the transmitter or transmitters. The actuator is responsive to signals received from the control computer to apply electrical currents through each transmitter as specified by the control computer. Desirably, the control computer is linked to the sensing units and arranged to operate each sensing unit to detect a field characteristic during the appropriate sensing interval of each actuation sequence. The control computer desirably is operative to vary the magnetic field strengths applied by the various transmitters during each cycle depending upon magnetic field characteristics detected by the sensing elements or sensors during one or more previous cycles. The control computer may also be operative to group and ungroup sensors or sensing elements as discussed above and to reorder sensing intervals as discussed above so that each transmitter is actuated with an ordered series of field strengths during the sensing intervals of each plural valued actuation sequence.

These and other objects, features and advantages of the present invention will be more readily apparent from the detailed description of the preferred embodiment set forth below, taken in conjunction with the accompanying drawings.

BRIEF DESCRIPTION OF THE DRAWINGS

FIG. 1 is a diagrammatic prospective view depicting portions of apparatus in accordance with one embodiment of the invention.

FIG. 2 is a fragmentary, diagrammatic prospective view depicting a portion of the apparatus illustrated in FIG. 1.

BEST MODES FOR CARRYING OUT THE INVENTION

Figure 3:
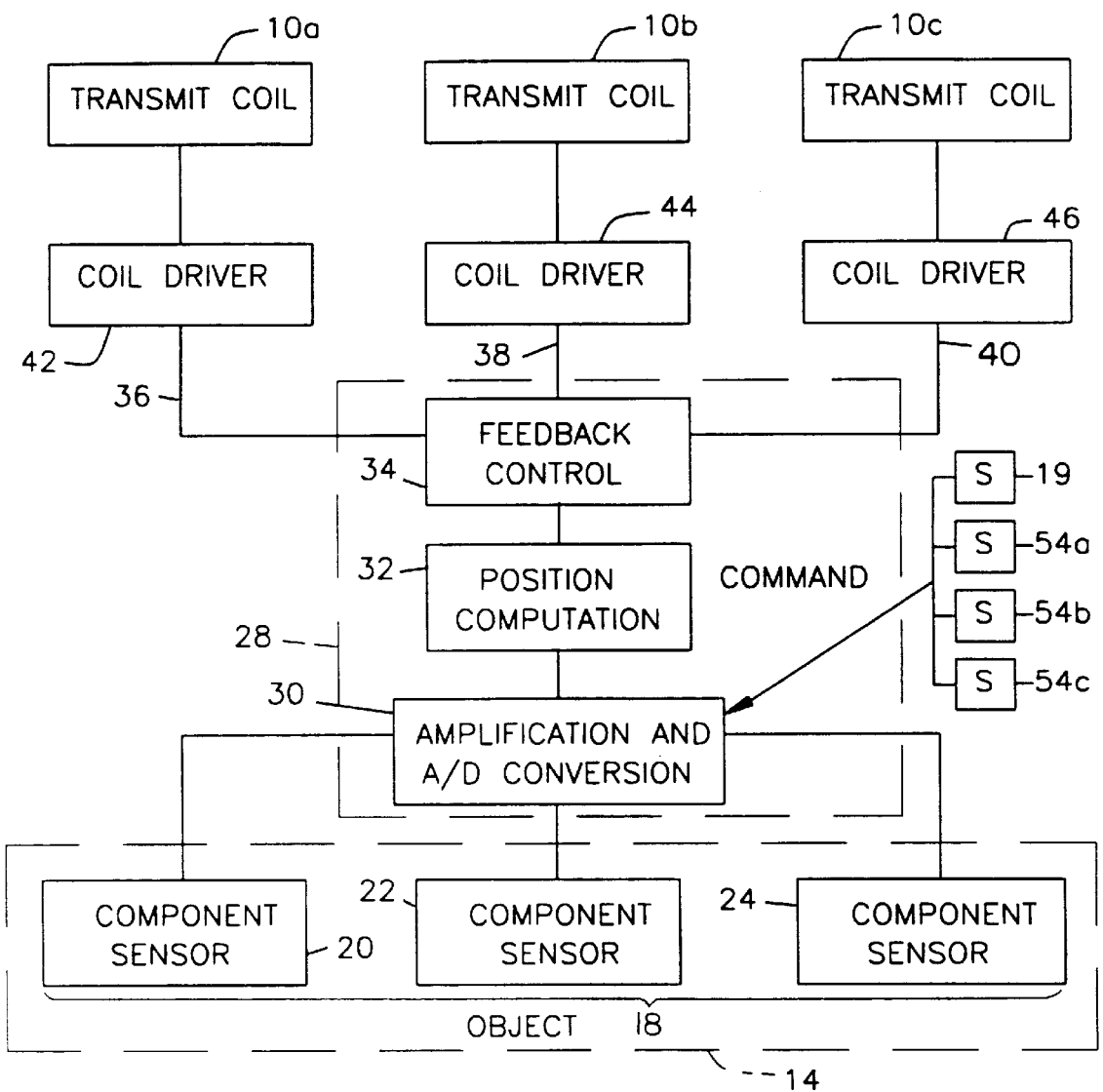
FIG. 3 is a functional block diagram depicting further portions of the apparatus depicted in FIGS. 1 and 2.

Apparatus in accordance with one embodiment of the present invention includes three generally helical transmitter coils 10 disposed in a common plane. Coils 10 are mounted in fixed position in the frame of reference of patient receiving bed 12. That frame of reference is denoted by a Cartesian coordinate system X, Y, Z as shown in FIG. 1. A patient P may be positioned on the patient receiving bed. The axes 11 of the coils are parallel to one another. A patient receiving bed 12 extends just above the plane of coil 10. The apparatus further includes an object or probe 14. The probe is adapted to be inserted into a medical instrument such as a catheter 16 and positioned at a desired location in the catheter, such as at the distal tip of the catheter or at another location along the length of the catheter. Probe 14 has mounted thereon a sensor 18. The system also includes another sensor 19 of the same type as sensor 18 mounted on a further object or probe 21, such as a catheter, endoscope or another medical instrument to be located. Still further sensors 54a, 54b and 54c are mounted on fiducal markers. As described in the aforementioned International Publication WO95/09562, a plurality of fiducial markers may be utilized to determine the location of the patient's body in the frame of reference of the patient-receiving bed, and to provide correlation between the frame of reference of the magnetic locating system and the frame of reference of previously-acquired image information. Each fiducial marker may include a sensor body 52, a tag 53 and a sensor 54 of the same type as sensor 18 releasably connected to the sensor body.

As all of the sensors 18, 19, 54a, 54b and 54c are identical in structure and function, only sensor 18 is described in further detail. It should be appreciated, however, that the description of sensor 18 is applicable to each of the other sensors as well. Sensor 18 includes three individual sensing element or component sensors 20, 22 and 24 adapted to sense components of the magnetic field in mutually orthogonal local directions X', Y' and Z'. That is, component sensor 20 is sensitive to magnetic fields directed in direction X', but largely insensitive to fields in directions Y' and Z', whereas component sensor 22 is sensitive only to fields in direction Y' and component sensor 24 is sensitive to fields in direction Z'. These component sensors are adapted to provide separate sensor signals representing the separate components. Sensor 18 may be a solid state sensor of the type described in the aforementioned International Patent Publication WO95/09562, the disclosure of which is hereby incorporated by reference herein. As further described therein, each of the sensing elements or component sensors may include a generally planar magnetically sensitive film, such as a magneto-resistive film or a Hall effect sensing film. Each such film may be sensitive to fields directed in a preselected direction relative to the film. Alternatively, sensor 18 may include an array of miniature coils, the axes of the coils being oriented orthogonal to one another. Although these represent the preferred sensors, essentially any other magnetically sensitive device may be employed as, for example, magneto-optical sensors and flux gate magnetometers.

Component sensors 20, 22 and 24 are connected through a cable 26, with separate leads for each sensor, to a command unit 28. Command unit 28 (FIG. 3) includes an input amplification and analog to digital ("AID") conversion section 30 adapted to receive the individual signals from component sensors 20, 22 and 24 of sensor 18, amplify the same and convert the same to digital form. The amplification and A/D conversion unit 30 may also include other conventional signal processing devices such as analog or digital band pass filtering and noise rejection devices and signal averages. Each of the other sensors 19, 54a, 54b and 54c is linked to the input amplification and analog to digital conversion section 30 in the same manner, through additional separate leads (not shown) connecting the individual sensing elements or component sensors of the other sensors to section 30. Section 30 is arranged to acquire signals from one sensor at a time.

Command unit 28 further includes a computation unit 32. Computation unit 32 may be implemented as a programmed general purpose computer. As further discussed below, the position computation unit is arranged to compute the disposition of each sensor 18, 19, 54a, 54b and 54c from the sensor signals acquired from that sensor. The disposition of the sensor also indicates the disposition of the object attached to the sensor in question. For example, the disposition of sensor 18 indicates the disposition of the object or probe 14 at the catheter tip from the sensor signals. As used in this disclosure, the term "disposition" of an element refers to the position of the element, the orientation of the element or both. Thus, the computation unit is arranged to calculate the position of each sensor, the orientation of the sensor, or, preferably, both position and orientation. Command unit 28 may be linked to a display device (not shown) for providing a human intelligible representation of the position of the probe or object 14. Such human intelligible representation may be provided either as numerical information presenting the position and/or orientation of object 14 in the X, Y, Z coordinate system or, preferably, as a pictorial representation of the object and of the associated catheter superposed on a pictorial representation of the patient.

Command unit 28 further includes a control unit 34. Control unit 34 is linked by output lines 36, 38 and 40 to three separate coil drivers 42, 44 and 46. Each coil driver is linked to one of the transmitter coils 10. Each coil driver is adapted to send a direct current through the associated transmit coil 10. Each coil driver is arranged to control the amplitude of such current, and to turn the current on or off, in response to control signals received from control unit 34. The control unit is arranged to signal the coil drivers to provide currents to their respective transmit coils in sequence as specified by the control signals received from control unit 34 as further described below, so that coil 10a receives current while coils 10b and 10c are inactive; coil 10b receives current while coils 10a and 10c are inactive and coil 10c receives current while coils 10a and 10b are inactive. The control unit also actuates the coil drivers to vary the amplitude of the current to each coil as discussed below, in response to signals form- computation unit 28. Control unit 34 may include conventional interface devices such as-digital to analog converters or bus interface units so that the output of the control unit is compatible with the control input of each coil driver. Also, although the control unit is illustrated separately from the other logical units of command unit 28, it should be appreciated that the control unit may share physical elements of the command unit and other elements. For example, where the command unit incorporates a general purpose computer, the processor of the computer may serve both as an element of the position computation unit and as an element of the control unit, executing functions appropriate to the different units at different times.

In a method according to one aspect of the invention, a catheter 16 is advanced into the body of a patient P. The probe 14 with sensor 18 thereon is disposed at the tip of the catheter. The catheter tip is disposed at an unknown location somewhere above the plane of coils 10. Likewise, sensor 19 on device 21 is disposed at a different unknown location, and sensors 54a, 54b and 54c are disposed at still other unknown locations.

Control unit 34 actuates the coil drivers in cyclic operation. Each cycle includes a null period, during which the control unit commands the coil drivers 42,44,46 to provide zero current to all coils. During this null period, the amplification and conversion unit 30 acquires null signal samples form each component sensor 20, 22 and 24. These null signal samples represent background magnetic fields in the vicinity of the system. Each cycle also includes a setting sequence. In the setting sequence, the control unit commands the coil drivers to actuate each coil in turn using an initial or default value for the current amplitude to be provided to each coil 10. Amplification and conversion unit 30 samples the signal from each of the sensing elements or component sensors 20, 22 and 24 of sensor 18, and from each of the sensing elements in each of the other sensors 19, 54a, 54b and 54c, at a preselected time after the beginning of current flow through each coil. For example, at a prese-lected time after the beginning of current flow through transmit coil 10a, unit 30 takes a sample of the signal from each of component sensors 20, 22 and 24, and converts the same to digital format. Command unit 28 then calculates a total field magnitude for sensor 18 based upon these individual signals. The total field magnitude is:

$$|B_{18-10a}| = \sqrt{(k_{20}S_{20})^2 + (k_{22}S_{22})^2 + (k_{24}S_{24})^2}$$

where: $B_{18-10a}$, is the magnitude of the magnetic field vector at sensor 18 at the time that coil 10a is actuated;

$K_{20}$ is a sensitivity factor relating the signal strength from sensor 20 to the magnetic field component along axis X';

$S_{20}$ is the signal strength from sensor 20 during the actuation; and $K_{22}$, $S_{22}$ and $K_{24}$ and $S_{24}$ are similar sensitivity constants and signal strengths for the other sensors 22 and 24.

In like manner, the system computes a total field magnitude for each of sensors 19, 54a, 54b and 54c during actuation of coil 10a. The system similarly actuates coils 10b and 10c in order, using the default current strength. Here again, the system computes the magnitude of the total field vector prevailing at each sensor during actuation of coil 10b and independently computes the magnitude of the total field vector prevailing at each sensor during actuation of coil 10c.

After detecting the component signals and calculating the total field magnitude prevailing at each sensor during actuation of each coil during the setting sequence, the control unit determines the coil currents or field strengths applied during the measurement sequence which will follow later in the cycle. These coil currents or field strengths are calculated to provide field magnitudes at each sensor lying within a preselected range of magnitudes. This preselected range is chosen to lie within the optimum operating range of the sensor. Thus, the minimum field magnitude is selected to lie well above the noise threshold of the system and above the minimum sensitivity level of the sensor, where the maximum field level is selected to lie well below the maximum limit of linearity of the sensor, and well below the maximum field which the sensor can tolerate without loss of accuracy. For a typical amorphic type of magneto-resistive sensor, which is most accurate and repeatable when used with fields of less than about 4 Gauss, the preselected range of field magnitudes may be from about 1.0 to about 2.5 Gauss, With typical Hall effect sensors, which are most accurate when used with fields over about 30 Gauss, the preselected range will be above about 30 Gauss. For example, where probe 14 and sensor 18 are relatively close to coil 10a, the total field magnitude detected at sensor 18 when coil 10a is actuated in the setting sequence will be above the preselected range. Control unit 34 therefore will command coil driver 42 to operate coil 10a with a lower current, and hence lower field strength, during the measurement sequence to follow later in the cycle. Conversely, if sensor 19 is relatively far from coil 10a, the field magnitude sensed by sensor 19 during actuation of coil 10a with the default current value in the setting sequence will be below the preselected range. Control unit 34 therefore will instruct coil driver 42 to actuate coil 10a with a higher current, and hence higher field strength, during a different sensing interval within the measurement sequence to follow later in the cycle. The adjustment may be proportional. For example, if the field magnitude sensed by sensor 19 in the setting interval, using the default current in coil 10a, is 0.1 times the minimum of the preselected range, the system may actuate coil driver 10*a* with a current 10 times the default current during the sensing interval of the measurement sequence.

In the same way, the system adjusts the field strength to be applied by each coil during the measurement sequence within a sensing interval associated with each sensor based upon the signals from the particular sensor observed during activation of that coil in the setting sequence of the cycle. Stated another way, the system maintains a list for each coil. Each list includes a separate field strength value associated with each sensor, to be applied by that coil during the measurement interval to follow later in the cycle. The lists constitute a matrix of field strength values, with one entry for each combination of one coil and one sensor. The field strength values are continually updated after the setting sequence of each cycle. Because the field strength produced by a coil is directly proportional to the current passing through such coil, the field strength values also constitute values of currents to be applied to each coil.

Before the measurement interval of each cycle, the command unit sorts the list of updated field strength values or currents to be applied to each coil into ascending order, and reorders the sensing intervals for the associated sensors to match the sorted list. The system also tests the field strength values or currents to determine if two or more field strength values lie within a preselected threshold range of one another. If so, the system combines the sensing intervals which employ those values, and selects a single value for use in the combined sensing interval so that the single value is also within the preselected range of with respect to all of the values for the combined sensing intervals. Thus, the average all of the field strength values for the intervals which were combined may be employed as the single field strength value for the combined interval. For example, the list of field strengths (stated in terms of current) to be applied by coil 10*a* may be as follows:

| Field Strength, stated as Current (milliamperes) | Apply during the sensing interval associated with the following sensor |
|---|---|
| 450 | 19 |
| 300 | 54a |
| 310 | 18 |
| 200 | 54b |
| 600 | 54c |

Assuming that the threshold field strength difference is 20 ma, the values of 300 and 310 associated with the sensing intervals for sensors 54*a* and 18 in the above sequence differ from one another by less than the threshold difference. After sorting and combining the sensing intervals associated with sensors 54*a* and 18, the list is as follows:

| Field Strength, stated as Current (milliamperes) | Apply during the sensing interval associated with the following sensor |
|---|---|
| 200 | 54b |
| 305 | 54a and 18 |
| 450 | 19 |
| 600 | 54c |

The sorted and combined list sets out a plural-value actuation sequence for coil 10*a*, i.e., a series of different field strengths to be applied to the coil during a series of sensing intervals within the measurement sequence of the cycle, and the sensor or sensors to be actuated during each such sensing interval. The sensing intervals incorporated in the actuation sequence are ordered in accordance with the field strengths to be applied during such sensing intervals. In the same way, the command unit arrives at an actuation sequence for each of the other coils. The number of sensing intervals in the actuation sequence assigned to each coil will depend upon the number of sensing intervals combined with one another. Where all of the sensing intervals for a particular coil are combined with one another, the actuation sequence for that particular coil will be a single-value actuation sequence, including only one field strength value.

The duration of each sensing interval is preset, and preferably corresponds to the minimum time required for amplification and conversion unit 30 to acquire data from a sensor or sensors, assuming that the sensor is disposed in a stable magnetic field and that the sensor has settled to a steady-state condition. The system supplements each actuation sequence with a starting transition interval preceding the first sensing interval, a terminal transition interval after the last sensing interval in the sequence. The system further supplements each plural-value actuation sequence with a middle transition interval between each pair of successive sensing intervals. The duration of the starting transition interval is selected to allow sufficient time for the current through the coil to increase from zero to approximately the current required in the first sensing interval, for eddy currents induced by the change in magnetic field from the coil to dissipate, and for the sensor to stabilize. Stated another way, the duration of the starting interval represents the time delay from the time the coil driver is commanded to change the field strength from zero to the first field strength to the time the sensor reading has settled to within a preselected error margin of the value which it would have during continuous actuation of the coil at the first field strength value. Similarly, each middle transition interval represents the time required for settling of the sensor reading after the coil driver is commanded to increase the field strength from the field strength used in the preceding sensing interval to the field strength used in the next succeeding sensing interval. The terminal transition interval represents the time required for the settling of the sensor reading when the field strength is decreased from that used for the last sensing interval in the actuation sequence to zero. The time required for each transition interval is directly related to the magnitude of the difference in field strengths before and after the sensing interval. The required time can be approximated by the formula:

$$t = A \ln |F_{after} - F_{before}|$$

Where:

t is the transition time;

A is a proportionality constant;

$F_{after}$ is the field strength or current after the transition interval;

$F_{before}$ is the field strength or current before the transition interval.

Figure 4:
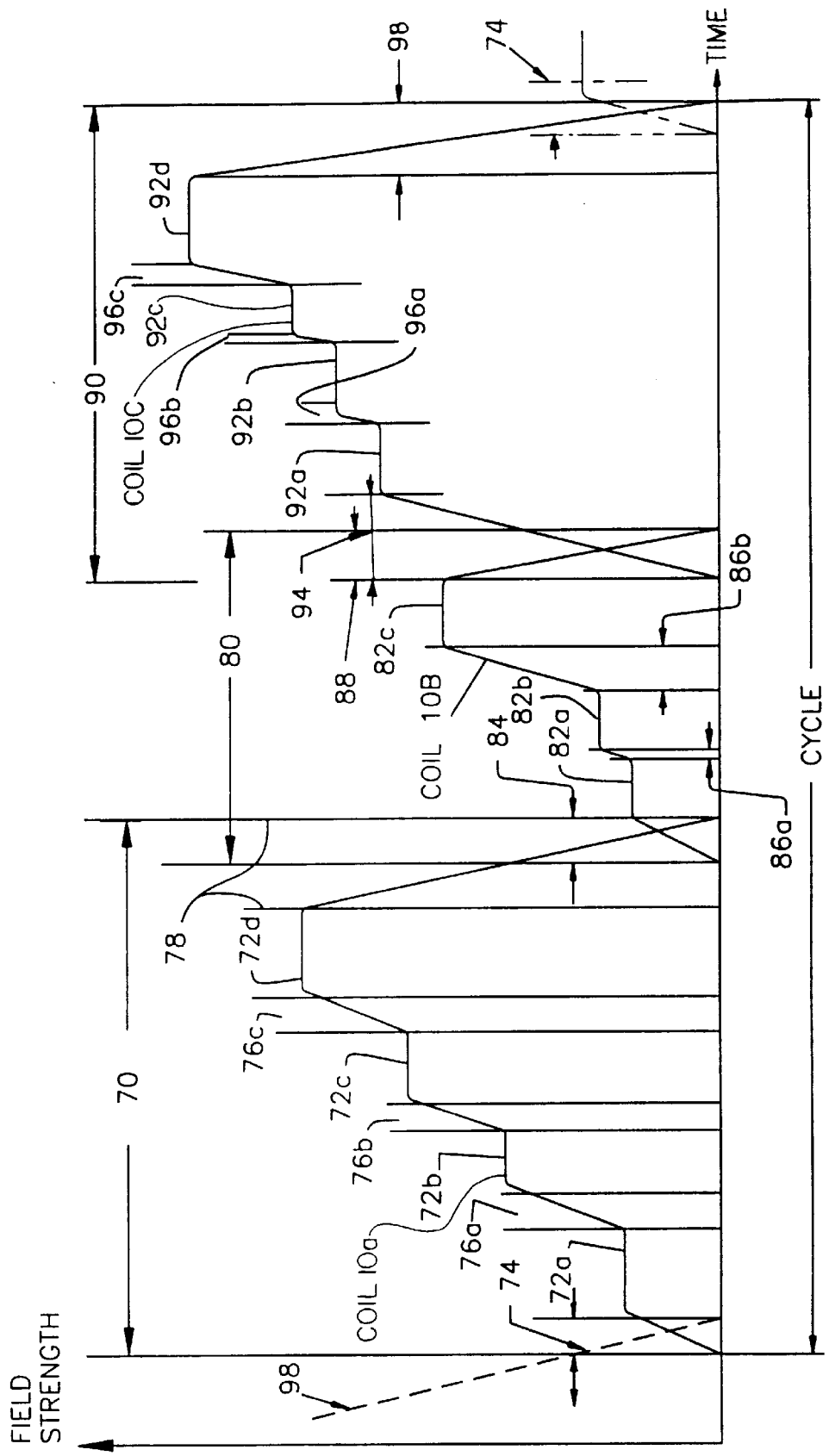
FIG. 4 is a graph depicting field strengths in a method according to one embodiments of the invention.

Feedback control unit 34 arranges the actuation sequences for the various coils in sequence with one another, to provide a complete schedule for the measurement sequence of the cycle, and operates coil drivers 42,44,46 to actuate the coils according to the schedule. A typical schedule, diagrammatically illustrated in FIG. 4, includes actuation sequence 70 for coil 10*a*, incorporating four sensing intervals 72*a*, 72*b*, 72*c*, 72*d*, starting transition interval 74, middle transition intervals 76*a*, 76*b*, 76*c* between the sensing intervals, and terminal transition interval 78 following the last sensing interval. The sequence 80 for coil 10b includes three sensing intervals 82, an initial transition interval 84 and a terminal transition interval 88, whereas the sequence 90 for coil 10c includes similar sensing intervals 92, starting transition interval 94, middle transition intervals 96 and terminal transition interval 98.

Figure 5:
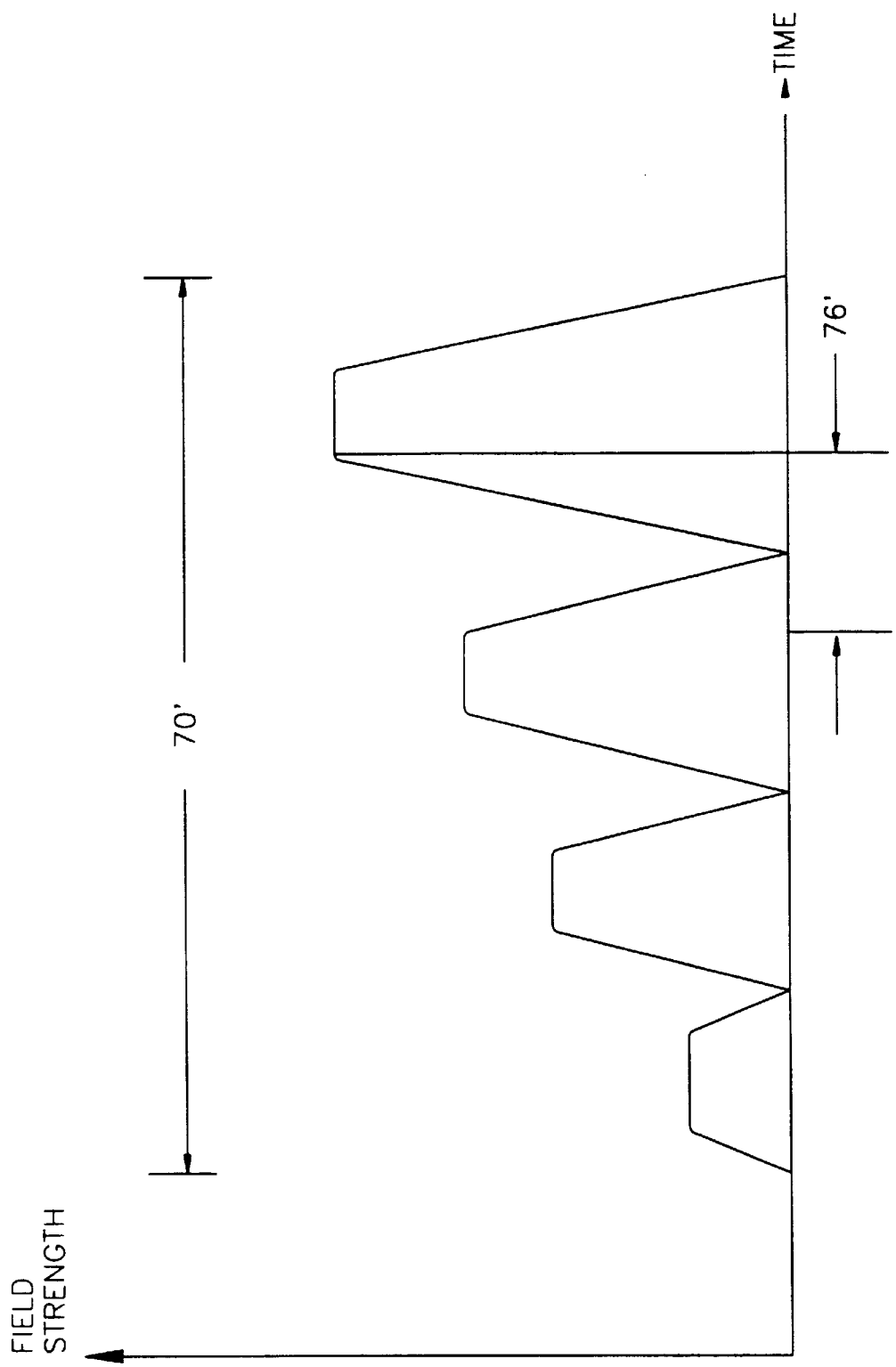
FIG. 5 is a graph similar to FIG. 4 but depicting a method not in accordance with the invention.

Within each actuation sequence, the field strength increases substantially monotonically from the beginning of the starting transition interval to the last sensing interval. The current or field strength is not reduced to zero after each sensing interval, but instead increases progressively to the value required for the next sensing interval. Therefore, each middle transition interval need only be long enough to accommodate the relatively small change in current or field strength between successive sensing intervals. The time saving afforded by this arrangement is apparent by comparison of sequence 70 with a comparable sequence 70' depicted in FIG. 5. Sequence 70' includes the same currents or field strengths used in sequence 70, but allows the field strength to drop back to zero between successive sensing intervals. Accordingly, sequence 70' requires considerably longer intervals 76' between successive sensing intervals.

Based upon the sensor signals acquired during the sensing intervals of the measurement sequence, and the known values of field strengths applied by the coils during each sensing interval, the system calculates the position and orientation of the sensor using conventional position finding algorithms. For example, the mathematical methods disclosed in U.S. Pat. No. 4,710,708 for finding positions using a multiple transmitting or receiving stations and a multi-axis sensor can be employed. The disclosure of said '708 patent is hereby incorporated by reference herein. Briefly, the magnitude of the fields in each of the local or sensor directions X', Y', Z' represented by each of the component sensor signals from each of the component sensors 20, 22 and 24 is a function of the overall strength of the field from the coil (also referred to as the magnetic dipole moment of the coil), the distance from the particular coil to the sensor and the sensor rotation angles, i.e., the angles between the local directions X', Y' and Z' and the coil frame of reference directions X, Y and Z. When three component sensor readings are collected during actuation of three separate coils and equated with the component strength, expressed as a function of location for fields from a particular coil, they form a system of nine equations with six unknowns (the X, Y, Z location of the sensor and the three rotation angles). The derivation of these equations is set forth in Appendix A. That system of equations can be solved by iterative methods such as the method of Marquardt or the method of Broyden for least-squares solution of an overdetermined system of non-linear equations. The command unit then provides output indicating the position and orientation of the sensor and hence indicating the position and orientation of the object connected to each sensor in the X-Y-Z Cartesian coordinate system of the coils.

The cycles discussed above are repeated. During operation, as the physician utilizes the system, the positions of one or more sensors may change. Any such change in position can cause the field magnitudes detected during the setting sequence of a subsequent cycle to change, whereupon the system will readjust the currents to be used by the coils during the measurement sequence of the new cycle. The system recomputes the actuation sequence to be applied during the measurement sequence of the new cycle. As the feedback control unit readjusts the field strengths, the altered values of current are translated into new values for field strengths from the individual coils which are used in the aforementioned position determining equations. In this manner, the system assures that during the measurement sequence of each cycle, the sensor is always exposed to a field having a magnitude within the preselected range wherever the sensor is placed within a sensing volume 50 extending over a preselected region above the plane of coils 10. The exact size of sensing volume 50 will depend upon the breadth of the preselected field magnitude range and the dynamic range of coil drivers 42, 44 and 46, i.e., the degree to which the coil drivers can vary the currents. The size of sensing volume 50 within which the sensor will receive fields within the preselected field magnitude range from all coils will also depend upon the positions of the coils. However, for a typical system having three coils spaced at vertices of an equilateral triangle with sides about 40 cm long, the sensing volume includes a region extending upwardly about 60 cm from the plane of the coils. At the plane of the coils, the sensing volume extends about 20 cm beyond the equilateral triangle bounded by the coils.

The system may be arranged to execute more than one null period during each actuation cycle. Where the aggregate time required for the actuation sequences to be applied to the various coils during a given cycle exceeds a threshold duration, the computer may automatically actuate the system to execute an additional null period and acquire new null signals between actuation sequences of a single cycle. This assures that the null signals are updated frequently, as may be required to compensate for rapidly changing background magnetic fields. In a further variant of the system described above, the system may compute the field strengths to be applied by each coil during the measurement sequence of the next cycle based upon signals obtained from each sensor during the sensing intervals of the measurement sequence in the previous cycle. In this variant, the system does not execute a setting sequence after the first cycle. Instead, the system tracks the field magnitudes observed at each sensor during the measurement sequences. If one or more of the field magnitudes for a particular sensor is out of the preselected range, the system does not calculate the position and orientation for that sensor. Instead, control unit 34 chances the field strength of the coil or coils associated with the out-of-range field magnitude for each sensor. For example, where probe 14 and sensor 18 are relatively close to coil 10a, the total field magnitude detected at sensor 18 when coil 10a is actuated will be above the preselected range. Control unit 34 therefore will command coil driver 42 to operate coil 10a with a lower current, and hence lower field strength, during a sensing interval within the measuring sequence of the next actuation cycle, and will command amplification and conversion unit 30 to acquire data from sensor 18 during that particular sensing interval. Conversely, if sensor 19 is relatively far from coil 10a, the field magnitude sensed by sensor 19 during actuation of coil 10a with the default current value will be below the preselected range. Control unit 34 therefore will instruct coil driver 42 to actuate coil 10a with a higher current, and hence higher field strength, during a different sensing interval within measuring sequence of the next actuation cycle. The control unit will actuate amplification and conversion unit 30 to acquire data from sensor 19 during that sensing interval while ignoring the data from sensor 19 during the sensing interval associated with the low-strength actuation of coil 10a and data acquisition from sensor 18. The adjustment process continues during subsequent cycles. Thus, if the higher field strength applied by coil 10a during the sensing interval associated with sensor 19 in the second cycle still results in a field magnitude sensed by sensor 19 below the preselected range, the system will set a higher field strength value to be applied by coil 10a in the sensing interval associated with sensor 19 during the next cycle, and the adjustment process continues until the signals from sensor 19, during activation of coil 10a, indicate a field strength within the preselected range. The coil drivers may be arranged to vary the overall field strength or dipole moment of each coil stepwise, as by varying the current stepwise. Each increase or decrease commanded by control unit 34 may be one step. Alternatively, the control unit can calculate an increase or decrease proportional to the degree to which the total field magnitude deviates from a target value within the preselected range. Thus, a relatively large change can be made when the field magnitude is far outside of the range, whereas a smaller change can be employed when the field magnitude is close to the range or within the range. To allow sufficient time for computation of the actuation sequences, the system may perform the computations required to set the actuation sequence for one coil in a later cycle while still executing the actuation sequences of an earlier cycle with another coil. For example, the actuation sequence for coil 10a in the next cycle can be calculated at any time after the actuation sequence for coil 10a is completed in the present cycle. While the system is executing the actuation sequence for coil 10a in the present cycle, it can calculate the actuation sequences for coils 10b and 10c in the present cycle.

As disclosed in the '380 application, certain sensors tend to lose accuracy when exposed to magnetic fields above a predetermined maximum. For example, certain magnetoresistive sensors temporarily lose accuracy if exposed to magnetic fields above about 4 Gauss. Where such sensors are employed in a multi-sensor system, the system should have appropriate provisions to avoid exposing sensors to excessive fields. The data from all sensors can be acquired during all of the actuation sequences, and control unit 34 can be arranged to increase coil currents in a progressive manner over several cycles when an increase is required. The data from sensors which are not used during a particular actuation sequence can be used to inhibit further increases if the field at the nominally unused sensor is approaching dangerous levels. Thus, if the system is in the process of progressively increasing the coil current in coil 10b to provide an adequate field level at sensor 18, the system may terminate such increases if the field magnitude at second sensor 54a during the reading cycle associated with first sensor 18 reaches the maximum level allowed at the second sensor. If this condition occurs while the field level at first sensor 18 is still below the preselected range, the system may display an error message or else may attempt to calculate position and orientation based on out-of-range sensor signal, or both. Alternatively, if the accuracy of the sensor can be restored, the data from the nominally unused sensors can be used to initiate restoration. For example, certain magnetoresistive sensors use a biasing magnetic field. If exposed to excessive fields, such sensors can be reset and restored to accuracy after the excess field is removed by adjusting a bias magnetic field applied within the sensor. The command unit may be arranged to trigger the reset process for one sensor if it is exposed to excess field during a cycle associated with another sensor.

In a further variant, the coil currents, and hence the strengths of the fields from the individual transmitters, can be adjusted to bring the field components detected by each individual component sensor to within a preselected range. In such a system, each coil is adjusted separately with respect to each sensing element or component sensor. Thus, the current to transmit coil 10a during a sensing interval associated with component sensor 20 is adjusted over several cycles to bring the individual sensor signal from component sensor 20, representing the field component magnitude in the local X' direction, into a preselected range. In this adjustment, the signals from the other component sensors 22 and 24 on the same sensor, and the signals from other sensors, are disregarded. This sequence of operations is repeated again with coil 10a for each of the other sensing elements on sensor 18 and for all of the sensing elements on the other sensors, and the whole process is repeated again for the other coils. After such adjustment the actuation sequence for each coil will include a separate sensing interval associated with each sensing element. However, where the field strengths required for plural sensing elements are within the threshold field strength difference of one another, the sensing intervals associated with plural sensing elements can be merged with one another so that the actuation sequence for a particular coil may include a lesser number of sensing intervals, and may include only one sensing interval. Thus, the system may treat either an entire sensor, or an individual sensing element, as a separate unit, and may establish separate sensing intervals for either type of unit. It is also possible to treat some complete sensors as units, while treating individual sensing elements of other sensors as units, so that some sensing intervals are associated with complete sensors, whereas other sensing intervals are associated with individual sensing elements. As used in this disclosure, the term "sensing unit" refers to both sensors and individual sensing elements.

Where the local direction associated with a particular component sensor is orthogonal, or nearly orthogonal, to the direction of the field produced by a particular coil at the sensor, it may be impossible to bring the component in that local direction into the preselected range without either exceeding the current capacity of the coil driver or producing a total field so strong as to impair one of the other sensors. In His instance, however, at least one of the other component sensors will receive a component having a magnitude in the preselected range of magnitudes. In this variant, the signal from all of the component sensors may be monitored during a cycle associated with a particular component sensor. The maximum current applied to the coil may be limited to avoid exposing any other unused component sensor to an excessive field component in its sensing direction.

In a further variant of this approach, the preselected range of magnitudes for the field component in any particular direction is narrowed to include only a single preselected value, preferably within the optimum range of accuracy of the particular component sensor. The feedback control system thus operates to adjust the coil currents until the field component magnitude is at such single value. The position and orientation are calculated in the same way as discussed above. This variant has the advantage that nonlinearity in the component sensor response cannot affect the accuracy of the system. Provided that it is known that a particular reading from the sensor corresponds to the preselected value of field component magnitude, deviation from a linear relationship between component magnitude and sensor reading at other values of the component magnitude will not impair the accuracy of the system.

Certain field sensors exhibit so-called "off-axis sensitivity". That is, the transfer function or relationship between field component magnitude along the sensitive axis of a particular component sensor and the reading from that component sensor varies when a strong field component orthogonal to such axis is present. Off-axis sensitivity can be corrected by using the readings from two component sensors to evaluate the magnitude of the field perpendicular to the sensitive axis of the third component sensor, and using that magnitude to determine a correction factor to be applied to the reading from the third component sensor.

Although the systems discussed above employ coil-type electromagnets, other types of electromagnets can be employed. Indeed, the same principles can be applied to systems which utilize field transmitters other than electromagnets and sensors other than magnetic sensors. However, the savings in actuation time are most significant where the field transmitters and sensors employed require significant risetime and/or settling time, as is the case with electromagnets. For example, systems which employ alternating fields such as radiofrequency (RF) fields, various RF transmitters may be actuated in sequence. The sensor may include one or more receiving antennas, each such antenna being connected to a receiver adapted to provide a signal corresponding to the amplitude of the RF signal received by the antenna. In such a system, appreciable risetime or settling time may be required for each transmitter-receiver pair to stabilize after actuation of the transmitter to change the amplitude of the transmitted RF. With respect to an alternating-field system such as an RF system, references to field strength should be understood as referring to the amplitude of the alternating field. In the systems described above, each coil or transmitter is kept at a zero steady-state field strength between actuation cycles. Steady-state field strength values other than zero can also be employed. As disclosed in the '380 application, the roles of the transmitter and sensors are reversed. That is, a probe or object may be equipped with electromagnets or transmitters, whereas the fixed reference frame system may include the sensors.

Numerous other combinations and variations of the features discussed above can be utilized without departing from the present invention. By way of example, the physical location and the number of transmitters or electromagnets can be varied. In general, the sensors and transmitters should define a plurality of transmitter-receiver pairs, each including one element on an object to be tracked and one element on the fixed frame of reference.

In a further variant, the system adjusts the output of the transmitters in response to the calculated disposition of the object being tracked, rather than directly in response to the component signals or total field magnitude signal. Thus, the system can initially operate with the default of current values; derive an initial reading of the position and orientation of the object and then use that initially determined position and orientation to calculate the desired setting for each coil to achieve the desired field levels at the sensor. Such desired setting is selected to yield the field within the desired magnitude range at the object, assuming that the object has the position and orientation found in the initial reading. On the next cycle, the so-calculated coil currents are utilized and the process is repeated. In a variant of this approach, the system can store a lookup table listing the appropriate coil currents for various combinations of object position and orientation. Using the initially determined position and orientation, the system retrieves appropriate coil-current values from the lookup table for use in the next cycle.

In the embodiments discussed above, the sensor is associated with a catheter. The same system can be used with other medical instruments as, for example, endoscopes and surgical instruments. The system can also be applied to determine the disposition of objects other than medical instruments. For example, it can be used in tracking an input device for a computer.

The following PCT applications, each of which names Biosense, Inc. as an applicant, are also incorporated by reference herein: PCT published application no. WO 97/29701 entitled Catheter Based Surgery filed on Feb. 14, 1997 in the Israeli Receiving Office; PCT published application no. WO 97/29699 entitled Intrabody Energy Focusing filed on or about Feb. 14, 1997 in the Israeli Receiving Office; PCT published application no. WO 97/29682 entitled Locatable Biopsy Needle, filed on or about Feb. 14, 1997 in the Israeli Receiving Office; PCT published application no. WO 97/29678 entitled Catheter Calibration and Usage Monitoring filed on Feb. 14, 1997 in the Israeli Receiving Office; PCT published application no. WO 97/29679 entitled Precise Position Determination of Endoscopes filed on Feb. 14, 1997 in the Israeli Receiving Office; PCT published application no. WO 97/29710 entitled Medical Probes with Field Transducers filed Feb. 14, 1997 in the United States Receiving Office; PCT published application no. 97/29684 Catheter with Lumen filed Feb. 14, 1997 in the United States Receiving Office; PCT published application no. WO 97/29683 entitled Movable Transmit or Receive Coils for Location System filed Feb. 14, 1997 in the United States Receiving Office; PCT published application no. WO 97/29709 entitled Medical Procedures and Apparatus Using Intrabody Probes filed Feb. 14, 1997 in the United States Receiving Office; and PCT published application no. WO 97/29685 entitled Independently Positionable Transducers for Location System filed Feb. 14, 1997 in the United States Receiving Office. The PCT published application no. WO 97/29700 entitled, Multi-Element Energy Focusing, filed Feb. 14, 1997 in the Israeli Receiving Office and naming Victor Spivak as applicant is also incorporated by reference herein.

As these and other variations and combinations of the features described above can be utilized without departing from the invention, the foregoing description of the preferred embodiments should be taken by way of illustration rather than by way of limitation of the invention as defined by the claims.

INDUSTRIAL APPLICABILITY

The present invention can be used in medical and related procedures.

APPENDIX A: CALCULATION OF POSITION AND ORIENTATION

The disclosure of which is hereby incorporated by reference herein.

Provided that we know the physical configuration of the field generator (transmitter) which is fixed in position during operation, the magnetic field detected by a sensor is a function of the position and orientation of the sensor. In our system field generator coils are stimulated sequentially. The field sensed by a sensor (3 component sensors per probe) can be expressed in terms of position in x, y, z and orientation $\alpha, \beta, \gamma$ (roll, pitch and yaw respectively) i.e.:

$$B[\text{sensor}][\text{coil}] = f[\text{sensor}][\text{coil}](x, y, z, \alpha, \beta, \gamma)$$

Where [sensor] designates a particular sensor and [coil] designates a particular transmitter coil.

If the real field the sensor measures when [coil] is on is B'[sensor][coil], then theoretically, B'[sensor][coil]=B[sensor][coil]

i.e.

B'[sensor][coil]−f[sensor][coil](x, y, z, α, β, γ)=0.0

Since we have 3 sensors and 3 coils, the total equations are 9 with 6 unknowns (x, y, z for probe space location, α, β, γ for its orientation). By applying non-linear least square method, we can find unique x, y, z, α, β, γ for the probe.

Above shows the general ideal of the algorithm. In detail:

Assume the orthogonal X,Y,Z reference coordinate system (magnetic location Cartesian coordinate) is described by matrix $$e_l = \begin{bmatrix} e_{l11} & e_{l12} & e_{l13} \\ e_{l21} & e_{l22} & e_{l23} \\ e_{l31} & e_{l32} & e_{l33} \end{bmatrix}$$

the probe's orthogonal system is:

$$e_p = \begin{bmatrix} e_{p11} & e_{p12} & e_{p13} \\ e_{p21} & e_{p22} & e_{p23} \\ e_{p31} & e_{p32} & e_{p33} \end{bmatrix}$$

and, since the three sensors on probe may not be orthogonal to each other, their non-orthogonal axes can described as:

$$e_n = \begin{bmatrix} e_{n11} & e_{n12} & e_{n13} \\ e_{n21} & e_{n22} & e_{n23} \\ e_{n31} & e_{n32} & e_{n33} \end{bmatrix}$$

a transfer matrix T[i][j] which is to be used in later on calculation can be obtained from:

$T_{[i][j]} = e_{n[i]} \cdot e_{p[j]} \forall i,j \in \{1,2,3\}$ another matrix ortho_OV[i][j] which is to be used also can be defined as:

ortho_OV$_{[i][j]} = e_{l[i]} \cdot e_{l[j]} \forall i,j \in \{1,2,3\}$ since we use roll(α), pitch(β), yaw(γ) to define probe orientation, ortho_OV[i][j] can be also described by:

ortho_OV[1][1]=cos(α) cos(γ)−sin(α) sin(β) sin(γ)

ortho_OV[1][2]=cos(α) sin(γ)−sin(α) sin(β) cos(γ)

ortho_OV[1][3]=−sin(α) cos(β)

ortho_OV[2][1]=−cos(β) sin(γ)

ortho_OV[2][2]=cos(β) cos(γ)

ortho_OV[2][3]=sin(β)

ortho_OV[3][1]=sin(α) cos(γ)+cos(α) sin(β) sin(γ)

ortho_OV[3][2]=sin(α) sin(γ)−cos(α) sin(β) cos(γ)

ortho_OV[3][3]=cos(α) cos(β)

orthogonal vector matrix can therefore be calculated by matrix multiplication of previous defined matrix T and ortho_OV:

ov=T*ortho_OV

The theoretical magnetic field for an orthogonal system generated at sensor position pointing to $e_{l[i]}$ direction can be expressed as:

f[coil][i](x,y,z,α,β,γ)

(detail abbreviated), where f is a known function, and includes a dipole moment term having magnitude proportional to the current flow in the particular coil.

After non_orthogonality correction (sensors may not be perpendicular to each other), the magnetic field sensor measures should be:

$$B[sensor][coil] = \sum_{i=1}^{3} f[coil][i](x, y, z, \alpha, \beta, \gamma) \times OV^{-1}[i][sensor]$$

Assume the real field sensor detected when coil is on is B'[sensor][coil], then:

B'[sensor][coil]−B[sensor][coil]=0.0 therefore, the 9 equations to be solved for x, y, z, α, β, γ, are:

$B'$[sensor1] [coil1] −

$$\sum_{i=1}^{3} f[coil1][i](x, y, z, \alpha, \beta, \gamma) \times OV^{-1}[i][sensor1] = 0.0$$

$B'$[sensor1] [coil2] −

$$\sum_{i=1}^{3} f[coil2][i](x, y, z, \alpha, \beta, \gamma) \times OV^{-1}[i][sensor1] = 0.0$$

$B'$[sensor1] [coil3] −

$$\sum_{i=1}^{3} f[coil3][i](x, y, z, \alpha, \beta, \gamma) \times OV^{-1}[i][sensor1] = 0.0$$

$B'$[sensor2] [coil1] −

$$\sum_{i=1}^{3} f[coil1][i](x, y, z, \alpha, \beta, \gamma) \times OV^{-1}[i][sensor2] = 0.0$$

$B'$[sensor2] [coil2] −

$$\sum_{i=1}^{3} f[coil2][i](x, y, z, \alpha, \beta, \gamma) \times OV^{-1}[i][sensor2] = 0.0$$

$B'$[sensor2] [coil3] −

$$\sum_{i=1}^{3} f[coil3][i](x, y, z, \alpha, \beta, \gamma) \times OV^{-1}[i][sensor2] = 0.0$$

$B'$[sensor3] [coil1] −

$$\sum_{i=1}^{3} f[coil1][i](x, y, z, \alpha, \beta, \gamma) \times OV^{-1}[i][sensor3] = 0.0$$

$B'$[sensor3] [coil2] −

-continued $$B'[\text{sensor3}][\text{coil3}] - \sum_{i=1}^{3} f[\text{coil2}][i](x, y, z, \alpha, \beta, \gamma) \times OV^{-1}[i][\text{sensor3}] = 0.0$$

$$\sum_{i=1}^{3} f[\text{coil3}][i](x, y, z, \alpha, \beta, \gamma) \times OV^{-1}[i][\text{sensor3}] = 0.0$$

A well-known non-linear least squares equation solver can be applied to solve the above equations and find probe position x, y, z and orientation α, β, γ.

What is claimed is:

1. A method of operating a location system including at least one transmitter and a plurality of sensing units, the method including the steps of cyclically actuating said transmitters so that during each cycle of actuation, each said transmitter is actuated in a preselected actuation sequence and operating said sensing units to detect characteristics of fields impinging thereon during said actuation sequences, at least one said transmitter being actuated during at least some cycles in a plural-value actuation sequence to provide a field with different field strengths during a sequence of plural sensing intervals and with a progressively varying strength during middle transition intervals between sensing intervals, said progressively varying strength being greater than zero at all times during each middle transition interval.

2. A method as claimed in claim 1 wherein said progressively varying strength varies substantially monotonically during each said middle transition interval.

3. A method as claimed in claim 2 wherein the field strengths applied during the sensing intervals of each said plural-value actuation sequence are ordered progressively.

4. A method as claimed in claim 3 wherein the field strengths applied during the sensing intervals of each said plural-value actuation sequence are ordered from a lowest strength to a highest strength.

5. A method as claimed in claim 3 wherein the field strengths applied during the sensing intervals of each said plural-value actuation sequence are ordered from a highest strength to a lowest strength.

6. A method as claimed in claim 1 wherein, during at least some cycles, at least one said transmitter is actuated in a single-value actuation cycle to provide a single sensing-field strength during a single sensing interval.

7. A method as claimed in claim 6 further comprising the step of maintaining each said transmitter at a steady-state field strength during at least one null period in each actuation cycle and detecting null signals from each said sensing unit during each said null period.

8. A method as claimed in claim 7 wherein said steady-state field magnitude of each transmitter is zero.

9. A method as claimed in claim 7 further comprising the step of automatically providing at least one additional null period between actuation sequences in a cycle and acquiring additional null signals from said sensing units whenever the total duration of such cycle exceeds a threshold duration.

10. A method as claimed in claim 1 wherein said step of cyclically actuating said one or more transmitters includes the step of actuating each said transmitter with a predetermined field strength during a setting sequence within each cycle, the method further comprising the step of detecting one or more characteristics of the field detected by each sensing unit during each said setting sequence and adjusting the field strengths to be applied by each said transmitter during an actuation sequence within each cycle based upon the field characteristics detected by said sensing units during the setting sequence of that cycle.

11. A method as claimed in claim 1 further comprising the step of adjusting the field strengths applied by said transmitters during later cycles in response to field characteristics detected by said sensing units during earlier cycles.

12. A method as claimed in claim 11 further comprising the step of automatically combining sensing intervals associated with different sensors with the actuation sequence for a particular transmitter whenever the field strengths to be applied by the transmitter during plural sensing intervals differ from one another by less than a preselected threshold field strength difference.

13. A method as claimed in claim 6 wherein each said transmitter includes an electromagnet and wherein each said sensing unit includes one or more magnetic sensing elements.

14. A method as claimed in claim 13 wherein the field strength provided by each electromagnet is varied during each cycle by varying the magnitude of a current passing through such electromagnet.

15. A method as claimed in claim 13 wherein said step of operating said sensing units includes the step of operating each sensing unit to detect a field characteristic during a sensing interval of each said actuation sequence.

16. A method as claimed in claim 15 wherein each said sensing unit is a multielement sensor including a plurality of magnetic component sensors, and wherein each sensing interval is associated with one or more multielement sensors.

17. A method as claimed in claim 13 wherein each said sensing unit is a multielement sensor including a plurality of magnetic component sensors, and wherein each sensing interval is associated with one or more individual component sensors.

18. A method as claimed in claim 1 wherein said step of operating said sensing units includes the step of operating different sensing units to detect field characteristics during different sensing intervals of each plural-value actuation sequence.

19. Location apparatus including:
(a) at least one transmitter for transmitting a field;
(b) a plurality of sensing units operative to detect characteristics of fields impinging thereon;
(c) an actuator operative to actuate said transmitters cyclically so that during each cycle of actuation, each said transmitter is actuated in a preselected actuation sequence, and so that at least one said transmitter is actuated during at least some cycles in a plural-value actuation sequence to provide a magnetic field in a preselected direction with different sensing-field strengths during a sequence of plural sensing intervals and with a progressively varying strength during middle transition intervals between sensing intervals, said progressively varying strength being greater than zero at all times during each middle transition interval.

20. Apparatus as claimed in claim 19 wherein said actuator is operative to varying the field strength substantially monotonically during each said middle transition interval.

21. Apparatus as claimed in claim 20 wherein said actuator is operative to actuate the transmitters so that the field strengths applied during the sensing intervals of each said plural-value actuation sequence are ordered progressively.

22. Apparatus as claimed in claim 21 wherein said actuator is operative to actuate the transmitters so that the field strengths applied during the sensing intervals of each said plural-value actuation sequence are ordered from a lowest strength to a highest strength.

23. Apparatus as claimed in claim 22 wherein said actuator is operative to actuate the transmitters so that each said transmitter is maintained at a steady-state field strength during at least one null period within each cycle.

24. Apparatus as claimed in claim 22 further comprising a control computer, said actuator being connected to said control computer for receipt of control signals therefrom, said actuator being responsive to said control computer to apply drive each said transmitter as specified by said control computer.

25. Apparatus as claimed in claim 24 wherein said control computer is linked to said sensing units and said control computer operates said sensing units so that each sensing unit to detect a field characteristic during a sensing interval of each said actuation sequence.

26. Apparatus as claimed in claim 25 wherein said control computer is operative to vary the field strengths applied by each said transmitter during each cycle depending upon the field characteristics detected by said sensing units during one or more previous cycles.

27. Apparatus as claimed in claim 25 wherein said control computer is arranged to operate different sensing units to detect field characteristics during different sensing intervals of each plural-value actuation sequence.

28. Apparatus as claimed in claim 19 wherein each said transmitter includes an electromagnet.

29. Apparatus as claimed in claim 19 further said at least one transmitter includes a plurality of transmitters, the apparatus further comprising means for mounting said plural transmitters at a plurality of locations adjacent to a sensing volume.

30. Apparatus as claimed in claim 29 wherein said at least one sensor includes a multielement sensor having a plurality of said sensing elements disposed adjacent one another, each said sensing element in said multielement sensor being operative to detect the magnitude of a field component in a different local direction relative to said sensor.

* * * * *